United States Patent [19]

Sakane et al.

[11] Patent Number: 4,866,243
[45] Date of Patent: Sep. 12, 1989

[54] LASER APPLYING APPARATUS

[75] Inventors: Toshio Sakane, Sagamihara; Yasuyuki Numajiri, Kawasaki, both of Japan

[73] Assignee: Canon Kabushiki Kaisha, Tokyo, Japan

[21] Appl. No.: 186,944

[22] Filed: Apr. 27, 1988

[30] Foreign Application Priority Data

Apr. 30, 1987 [JP] Japan .................................. 62-107648
Apr. 15, 1988 [JP] Japan .................................. 63-092698

[51] Int. Cl.$^4$ ............................................ B23K 26/00
[52] U.S. Cl. .............................. 219/121.62; 128/303.1; 219/121.74; 219/121.83; 372/27
[58] Field of Search ...................... 219/121.67, 121, 72, 219/121.61, 121.62, 121.83, 121.74, 121.75, 121.68, 121.69; 128/303.1; 372/105, 106, 27, 26, 28

[56] References Cited

U.S. PATENT DOCUMENTS 4,394,764 7/1983 Ishikawa .............................. 372/26
4,580,557 4/1986 Hertzmann ................... 219/121 LA

*Primary Examiner*—C. L. Albritton
*Attorney, Agent, or Firm*—Fitzpatrick, Cella, Harper & Scinto

[57] ABSTRACT

A laser applying apparatus is provided with a laser source, setting means for setting the intensity of laser light applied to a portion to be irradiated, excitation means disposed in the laser source for selecting a stage of laser light intensity conforming to the set value by the setting means from among a plurality of stages of laser light intensity and causing it to be output from the laser source, and adjusting means disposed in the optical path for adjusting the intensity of the laser light output from the laser source to the intensity set by the setting means, by varying the light attenuation rate.

9 Claims, 4 Drawing Sheets

LASER APPLYING APPARATUS

BACKGROUND OF THE INVENTION

1. Field of the Invention

This invention relates to a laser applying apparatus, for example, a laser applying apparatus for ophthalmic operation using YAG laser light to treat a patient's eye to be examined.

2. Related Background Art

When carrying out an ophthalmic operation by the use of a YAG laser apparatus, a laser light of minimum output level which can provide a treatment effect must be applied to an eye to be examined in order to suppress the eye pressure of the eye to be examined from rising by the application of the laser light.

Also, the above-mentioned minimum output level which can provide a treatment effect differs greatly depending on the region of the eye to be examined and the substance of the treatment, and for example, several millijoules is required for the destruction of the front or rear pouch and several tens of millijoules is required for the excision of the iris. Therefore, in the conventional YAG laser apparatus for medical treatment, the output value of laser light output from a YAG laser source is fixed at a predetermined value equal to or greater than a maximum output level used during the treatment of the eye to be examined, and by changing the attenuation rate by the use of an attenuator, the output level of the laser light is adjusted to a minimum value which can provide a treatment effect.

YAG laser light has its refractive index distribution varied in conformity with the temperature distribution in the cross-section of a YAG rod, and the output of the laser light fluctuates as the resonance mode deviates. In a working machine or the like, the YA rod is water-cooled to thereby keep it at a constant temperature, whereby the deviation of the resonance mode and the fluctuation of the output of the laser light are prevented. However, the eye to be examined constantly vibrates about the fixation point, and in the YAG laser apparatus for medical treatment, it is necessary to follow the movement of the eye to be examined and always effect fine adjustment of the applied position of the laser light. Therefore, the water-cooling means for stabilizing the output as described above is difficult to adopt and it is usual with the conventional apparatus that air-cooling means is used for the YAG rod, and this leads to the problem that the intensity of the output of the laser light becomes unstable due to heat generation.

Also, as described above, in the conventional apparatus, laser light of maximum output level used is always produced and the output of the laser light is suitably attenuated by an attenuator, whereafter the laser light is applied to the eye to be examined and therefore, the energy efficiency is low and unnecessary heat is generated in the YAG laser source, and this also leads to the disadvantage that the intensity of the output of the laser light becomes more unstable.

SUMMARY OF THE INVENTION

It is an object of the present invention to provide a laser applying apparatus which is capable of applying laser light of stable output intensity conforming to the set condition to a portion to be examined.

It is another object of the present invention to provide a laser applying apparatus in which the output of a laser source is variable and the heat generation of the laser source is suppressed.

It is a further object of the present invention to provide a laser applying apparatus which is provided with illuminating means for observing an eye to be examined and in which when said illuminating means has come into the optical path of laser light for treatment, the output of the laser light is attenuated.

DESCRIPTION OF THE PREFERRED EMBODIMENTS

Figure 1:
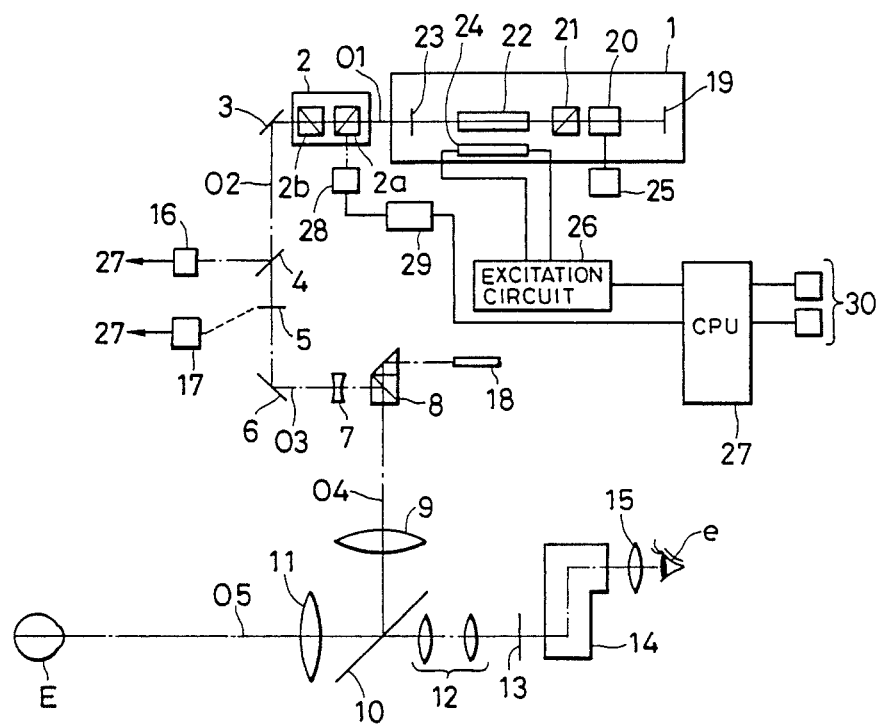
FIG. 1 shows a first embodiment of an ophthalmologic apparatus according to the present invention.

Referring to FIG. 1 which shows the construction of a first embodiment of the present invention, an attenuator 2 comprising two polarizers 2a and 2b, and a mirror 3 are provided in succession from a YAG laser source 1 along the optic axis 01. A half-mirror 4, a shutter 5 and a mirror 6 are disposed in succession along the optic axis 02 in the direction of reflection of the mirror 3. A concave lens 7 and a prism 8 are disposed along the optic axis 03 in the direction of reflection of the mirror 6, and a convex lens 9 and a half-mirror 10 are provided along the optic axis 04 in the direction of reflection of the prism 8. Further, an objective lens 11 is disposed along the optic axis 05 in the direction of reflection of the half-mirror 10, and an expanding optical system 12, an infrared ray cut filter 13, an image inverting optical system 14 and an eyepiece 15 are disposed in succession along the direction of the optic axis 05 from the objective lens 11 to the half-mirror 10. A photodetector 16 is disposed in the direction of reflection of the half-mirror 4, and a shutter driving circuit 17 is connected to the shutter 5. An optical fiber cable 18 for directing the light from an He-Ne laser source for alignment, not shown, is optically connected to the prism 8.

In the YAG laser source 1, there are provided a mirror 19, an electro-optical element 20, a polarizer 21, a YAG rod 22 and an output mirror 23 on the optic axis 01, and a stroboscopic lamp 24 is disposed sideways of the YAG rod 22. A pulse generator 25 is connected to the electro-optical element 20, and a CPU 27 is connected to the stroboscopic lamp 24 through an excitation circuit 26. The polarizer 2a of the attenuator 2 is connected to the CPU 27 through a motor 28 and driving means 29, and the photodetector 16, the shutter driving circuit 17 and a setting switch 30 are further connected to the CPU 27.

In the YAG laser source 1, the mirror 19 and the output mirror 23 together form an oscillator, and a light beam emitted from the stroboscopic lamp 24 is condensed on the YAG rod 22 through a condensing mirror. The electro-optical element 20 operated by a voltage pulse output from the pulse generator 25, with the polarizer 21, effects the operation of oscillating the Q switch of the YAG laser. The output intensity of the laser light of the YAG laser source 1 is determined by the density of $Nd^{3+}$ contained in the YAG rod 22, the Q switch effect by the electro-optical element 20 and polarizer 21, the loss in the oscillator comprising the mirror 19 and the output mirror 23, the intensity of the light emitted from the stroboscopic lamp 24, and the laser light emission pulse width by the life of the YAG rod at the upper laser level. The attenuator 2 is capable of varying the attenuation rate of the intensity of the laser light by the polarizer 2a of the two polarizers 2a and 2b being rotated by the motor 28.

In the thus constructed YAG laser apparatus for medical treatment, the YAG laser light emitted from the YAG laser source 1 has its intensity attenuated by the attenuator 2, whereafter it is reflected by the mirror 3 and enters the half-mirror 4. Part of the YAG laser light is reflected by the half-mirror 4 and detected by the photodetector 16, and the intensity signal of the YAG laser light is output to the CPU 27. On the other hand, most of the laser light passes through the half-mirror 4 to the shutter 5. When the shutter 5 is intercepting the optic axis 02, the YAG laser light is all intercepted and the laser light is not applied to an eye E to be examined. However, when the shutter 5 is not intercepting the optic axis 02, the YAG laser light is reflected by the mirror 6 and the diameter of the YAG laser light is expanded by the expanding optical system comprised of the concave lens 7, the prism 8 and the convex lens 9. Further, the YAG laser light is reflected by the half-mirror 10, whereafter it is applied to the eye E to be examined through the objective lens 11.

Also, at the same time, the laser light emitted from the He-Ne laser source, not shown, is directed by the optical fiber cable 18 and alignment thereof with the YAG laser light is effected in the prism 8, whereafter said laser light enters the objective lens 11 through the convex lens 9 and the half-mirror 10 and is imaged on the eye E to be examined at the same position as the YAG laser light. The reflected light of the He-Ne laser light from the eye E to be examined passes through the objective lens 11 and the half-mirror 10 and enters an observation optical system comprised of the expanding optical system 12, the infrared ray cut filter 13, the image inverting optical system 14 and the eyepiece 15, and is observed by an examiner e. Of the reflected light from the eye E to be examined, the reflected light of the YAG laser light is removed by the infrared ray cut filter 13 and therefore, the examiner e is protected against the YAG laser light. The examiner e can know the applied position of the YAG laser spot while looking at the position of the He-Ne laser spot on the eye E to be examined.

When operating this YAG laser apparatus for medical treatment, the examiner e moves the position of the YAG laser spot applied onto the eye E to be examined to a predetermined position while observing the position of the He-Ne laser spot. At this time, the shutter driving circuit 17 is intercepting the YAG laser light with the shutter 5 disposed on the optic axis 02 in accordance with the signal from the CPU 27. Subsequently, the setting switch 30 is depressed a plurality of times to thereby set the intensity of the YAG laser light applied to the eye E to be examined. Thereupon, the CPU 27 counts the number of times of the depression of the setting switch 30 and causes the stroboscopic lamp 24 to emit light through the excitation circuit 26 in accordance with a set value corresponding to the count value. Simultaneously therewith, the CPU 27 regulates the attenuation rate of the attenuator 2 through the driving means and the motor 28, and moves the shutter 5 to the outside of the optic axis 02 through the shutter driving circuit 17 to thereby direct the YAG laser light onto the eye E to be examined.

The output intensity of the YAG laser light applied by the YAG laser source 1 can be varied by numerous parameters, and of those parameters, the excitation intensity and the pulse width can be extraneously controlled relatively easily.

A specific example of exciting means for roughly regulating the aforementioned laser output will now be described.

Figure 2A:
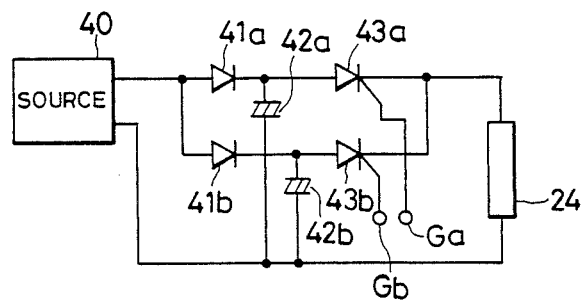
FIGS. 2A, 2B and 2C show some examples of a laser light excitation circuit.
Figure 2B:
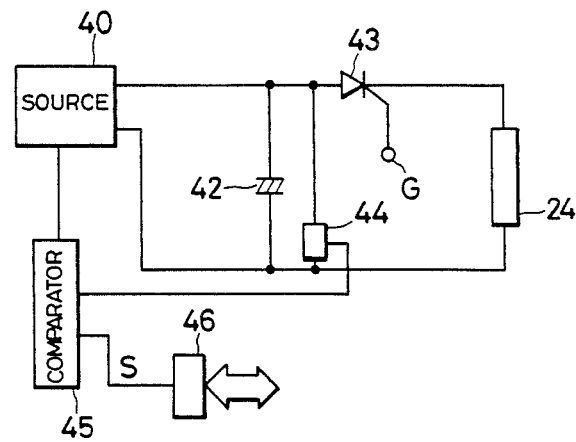
Figure 2C:
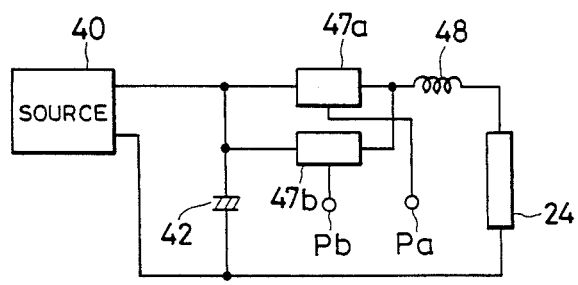

FIGS. 2A-2C show three examples of the excitation circuit 26 of the stroboscopic lamp 24 for oscillating a YAG laser light of two stages of intensity from the YAG laser source 1. In FIG. 2A, the output of a high voltage source 40 is connected to the anode terminals of diodes 41a and 41b, the cathode terminal of the diode 41a is connected to a capacitor 42a and a thyristor 43a, and the cathode terminal of the diode 41b is connected to the capacitor 42a and a thyristor 43b. The outputs of the thyristors 43a and 43b are both connected to the stroboscopic lamp 24, and a signal may be input from the CPU 27 to the gate terminals Ga and Gb of the thyristors 43a and 43b. One of the respective terminals of the high voltage source 40, the capacitors 42a and 42b and the stroboscopic lamp 24 is connected in common.

In such a circuit, the capacitors 42a and 42b are charged by the output of the high voltage source 40 through the diodes 41a and 41b, respectively, and a signal is input from the CPU 27 to one of the gate terminals Ga and Gb of the thyristors 43a and 43b, respectively, whereby the charge stored in the corresponding one of the capacitors 42a and 42b is discharged to the stroboscopic lamp 24. Thereby, the stroboscopic lamp 24 emits light, but the intensity of its emitted light differs depending on the amount of charge supplied from the capacitors 42a and 42b and therefore, by making the capacitors 42a and 42b different in capacity, the excitation level of the YAG rod 22 can be changed and thus, it becomes possible to select two stages of laser light intensity from the YAG laser source 1.

Referring to FIG. 2B which shows a second embodiment of the excitation circuit 26, the output of the high voltage source 40 is connected to the capacitor 42, the anode terminal of the thyristor 43 and a voltage divider 44. The cathode terminal of the thyristor 43 is connected to the stroboscopic lamp 24, the gate terminal G of the thyristor 43 is connected to the CPU 27, and the output of the voltage divider 44 is connected to a comparator 45. Also, the output of a D/A converter 46 is connected to the comparator 45, the output of which is connected to the high voltage source 40. Further, the output of the CPU 27 may be input to the D/A converter 46.

In this circuit, the output of the high voltage source 40 charges the capacitor 42 and the output voltage from the voltage divider 44 to the comparator 45 rises. At the same time, a reference voltage S is input from the CPU 27 to the comparator 45, through the D/A converter 46, and the comparator 45 compares the output voltage from the voltage divider 44 with the reference voltage S and turns on or off the output of the high voltage source 40 to thereby control the charging voltage level of the capacitor 42. When a signal is input from the CPU 27 to the gate terminal of the thyristor 43, the charge stored in the capacitor 42 is discharged to the stroboscopic lamp 24, which thus emits light. That is, by varying the reference voltage S, the amount of charge stored in the capacitor 42 can be changed. As described above, the intensity of the emitted light of the stroboscopic lamp 24 depends on the amount of charge supplied from the capacitor 42 and therefore, as a result, the excitation level of the YAG rod 22 can be changed and the intensity of the laser light of the YAG laser source 1 can be made variable.

Referring to FIG. 2C which shows a third embodiment of the excitation circuit 26, the output of the high voltage source 40 is connected to the capacitor 42 and pulsers 47a and 47b, and the outputs of the pulsers 47a and 47b are both connected to the stroboscopic lamp 24 through a coil 48. The output from the CPU 27 is connected to the respective terminals Pa and Pb of the pulsers 47a and 47b. The capacitor 42 and the coil 48 together constitute a pulse forming network (PFN) for generating a discharging pulse longer than the discharging pulse width in the stroboscopic lamp 24, and the pulsers 47a and 47b comprise a thyristor and a capacitor, respectively, and the charge begins to be discharged from the capacitor 42 to the stroboscopic lamp 24 in accordance with the signal input from the CPU 27 to the terminals Pa and Pb, and at a point of time whereat a predetermined amount of charge has been discharged, the discharge of the charge from the capacitor 42 to the stroboscopic lamp 24 is stopped.

In this circuit, the output of the high voltage source 40 charges the capacitor 42, and when in this state. a signal is input from the CPU 27 to the pulser 47a, the capacitor 42 starts to discharge through the coil 48 and the stroboscopic lamp 24 starts to emit light. When a signal is input to the control terminal Pb of the pulser 47b, the pulser 47b conducts and stop the discharging through the coil 48 and the light emission of the stroboscopic lamp 24 is terminated. That is, the pulse width of discharging is controlled by the time difference to the control terminals Pa and Pb, and any pulse width is obtained within the time range of PFN determined by the coil 48 and the capacitor 42.

Now, in the YAG laser source 1 of the light excitation type in which the emitted light of the stroboscopic lamp 24 is utilized to effect the excitation of the YAG rod 22, the variation in the quantity of emitted light of the stroboscopic lamp 24 with time and at each shot is unavoidable. The variation in the quantity of emitted light of the stroboscopic lamp 24 directly affects the variation in the output of the YAG laser source 1 and causes a decrease in the laser light output or a variation at each shot. The variation in the quantity of emitted light of the stroboscopic lamp 24 with time progresses gradually while, on the other hand, the fluctuation of the intensity of the YAG laser light at each shot is irregular and therefore, to reduce the deviation from the set value, means for estimating the intensity of the pulse of the YAG laser light to be applied next may be provided to thereby set the attenuation rate of the attenuator 2 matching the estimated value.

A specific procedure therefor will now be described in detail.

The output value of the current pulse of the YAG laser source 1 is calculated from the output of the photodetector 16 and the attenuation rate of the attenuator 2 by the CPU 27, and this output value is memorized in the memory portion of the CPU 27, and more specifically, output values corresponding to at least the past several pulses are memorized. The respective memorized output values corresponding to the past several pulses are weighted on the basis of an empirical rule obtained from an experiment and are simply averaged. The thus obtained average value is considered to be the output value of the pulse oscillated next, and the intensity of the light applied to the portion to be irradiated is estimated from the current attenuation rate of the attenuator 2.

When this estimated value differs from the set value, the attenuation rate of the attenuator 2 is varied to thereby correct the estimated value so as to coincide with the set value.

The present method of estimating the intensity of the light with a value converted into the output value of the laser source 1 need not change the intensity of the memorized past pulses even when the set value has been changed during the operation of the apparatus, and is usable in the same manner as during continuous outputting.

Also, when the memory portion of the CPU is blank as immediately after the main switch has been closed, the attenuation rate of the attenuator 2 is determined from the tentative output value predetermined on the memory and the set value, and outputting is tentatively effected with said attenuation rate after the shutter 5 is closed, and the tentative outputting is continued until said memory portion is filled up. At a point of time whereat the memory portion has been filled up, the shutter 5 is opened to thereby start the application of the laser light.

As described above, the excitation level of the YAG laser source is changed in conformity with the set value and heat generation is suppressed as much as possible and the variation with time and the fluctuation at each shot are estimate to finely regulate the transmission factor of the attenuator, whereby there can be provided a laser applying apparatus of stable output.

Figure 3:
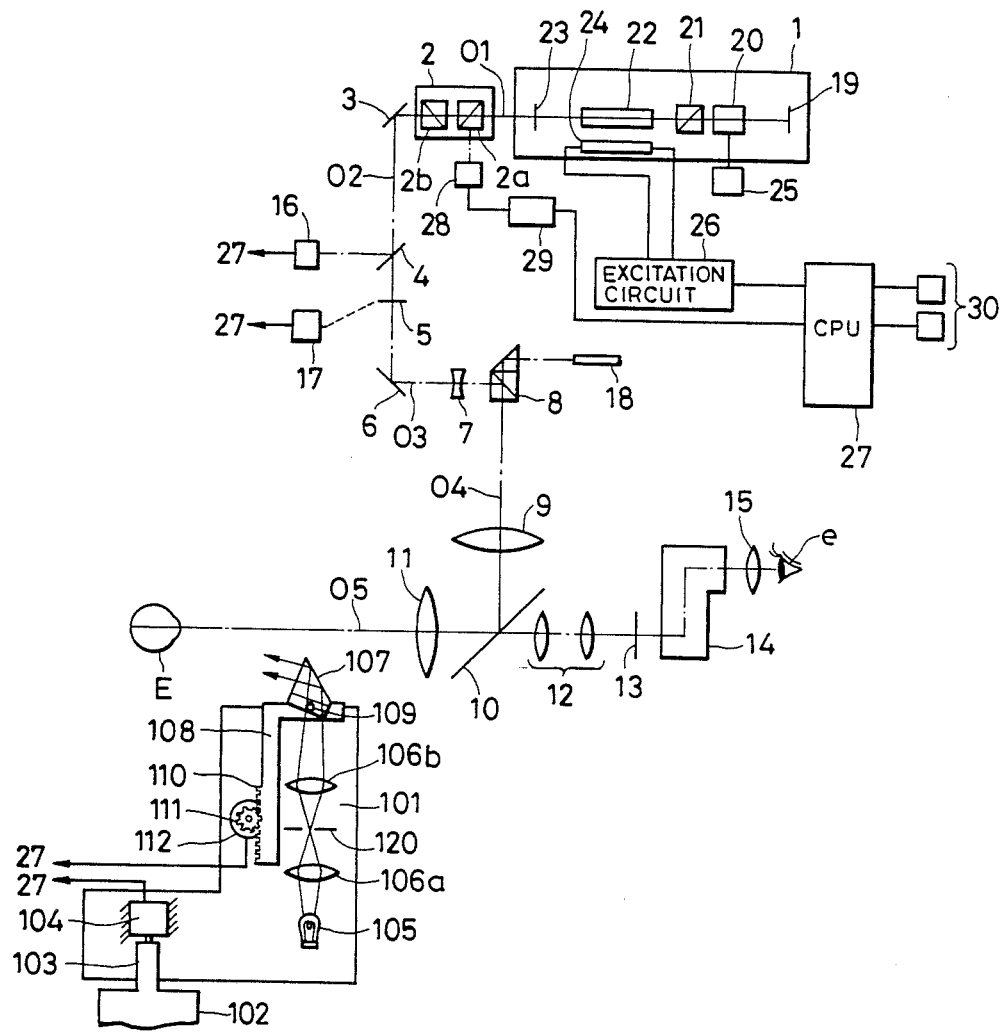
FIG. 3 shows a second embodiment of the present invention.

FIG. 3 shows a second embodiment of the present invention. In FIG. 3, reference numerals similar to those in FIG. 1 designate similar members. As compared with the first embodiment, the present embodiment is characterized in that a slit lamp illuminating portion for observing the eye to be examined is added.

Referring to FIG. 3, an illumination housing 101 is supported for rotation about a support shaft 103 fixed to a stage 102, and the angle of rotation of the illumination housing 101 may be detected by a first rotary encoder 104. A lamp 105 is installed in the illumination housing 101, and the light from the lamp 105 may pass through a lens 106a, a slit 120 and a lens 106b, may be reflected by a prism 107 for reflecting the slit illuminating light and may enter the eye E to be examined. The lens 106b is held for vertical movement along the optic axis thereof by a mechanism, not shown, and the prism 107 is installed for rotation about a rotary shaft 109 at the upper end portion of a vertically movable support arm 108 so that the illuminating position may not change. Although not shown, the vertical movement of the prism 107 and the vertical movement of the lens 106b are operatively associated with each other. A rack 110 is provided at the lower end portion of the support arm 108 and is in meshing engagement with a pinion 111 which is fixed to the shaft of a second rotary encoder 112 so that the angle of rotation thereof may be detected. The outputs of the first rotary encoder 104 and the second rotary encoder 112 are input to the CPU 27.

During the use of the apparatus, the light from the lamp 105 is projected onto the eye E to be treated through the lens 106a, the slit 120, the lens 106b and the prism 107 to enable the eye E to be treated to be observed.

Figure 4:
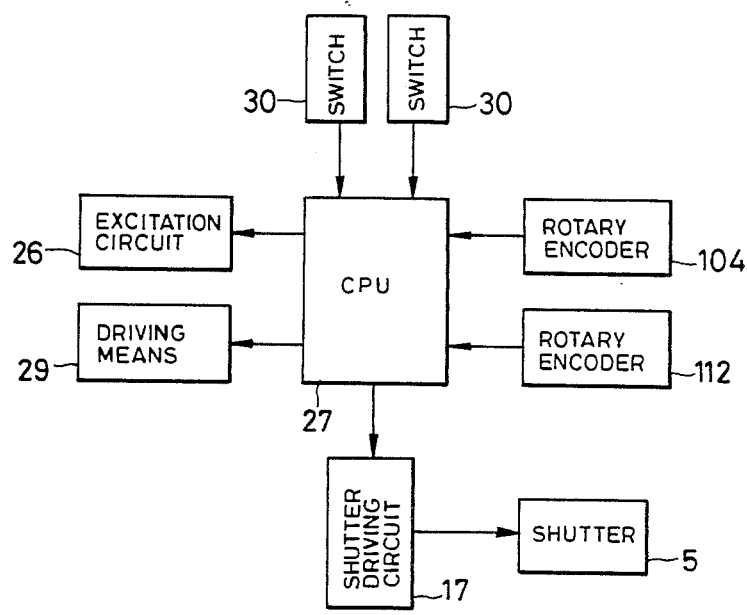
FIG. 4 shows electrical connections in the second embodiment.

FIG. 4 is a block diagram of a data processing unit for analyzing the position of the prism 107 on the basis of data detected from the first and second rotary encoders 104 and 112. The detected data may be transferred from the first and second rotary encoders 104 and 112 to the CPU 27. The excitation circuit 26, the driving means 29 and the shutter driving circuit 17 are connected to the CPU 27, and the shutter 5 is adapted to be operated by the shutter driving circuit 17.

In this embodiment, the angle of rotation of the illumination housing 101 in the horizontal direction can be detected by the first rotary encoder 104, whereby the displacement of the prism 107 in the horizontal direction can be known. Also, the angle of rotation of the pinion 111 can be detected by the second rotary encoder 112 and therefore, the amounts of vertical movement of the prism 107 and the lens 106b corresponding to the angle of rotation of the pinion 111 can be detected.

Figure 5:
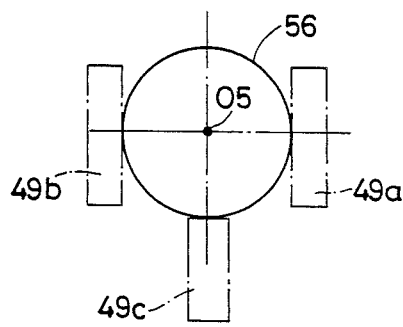
FIG. 5 shows the position limits of a prism for observation light.

Generally, the optical path of the laser light is fixed relative to the stage 102, and whether the prism 107 is within the light beam 56 of the laser light 05 inside position limits 49a, 49b and 49c as shown in FIG. 5 can be judged by the information of the angles of rotation of the illumination housing 101 and the pinion 111. So, the angle of rotation of the illumination housing 101 necessary for the prism 107 to be positioned in the boundary area between the optical path of the laser light 05 and the outside is found as by calculation, for example, at every plural angles of rotation of the pinion 111 and is memorized. The CPU 27 compares the angles of rotation of the illumination housing 101 and the pinion 111 supplied from the first and second rotary encoders 104 and 112 with the value of said memorized angle of rotation, and judges whether the prism 107 is within the light beam 56 of the laser light 05.

When the prism 107 is within the light beam 56, the CPU 27 supplies a signal to the excitation circuit 26 and the shutter driving circuit 17 to thereby reduce the output of the laser source and further operate the shutter 5, thereby intercepting the optical path. Thereby, heat generation of the laser source is prevented to thereby prevent the laser light from being applied to the eye E to be examined. Thus, the danger by the reflection of the laser light in an unforeseeable direction in the prism can be avoided.

In the foregoing, rotary encoders have been used to detect the angle of rotation of the illumination housing 101 and the angle of rotation of the pinion 111, but alternatively, variable resistors or the like may be used to monitor the position of the prism.

Also, there is conceived a method of using microswitches or the like to detect that the prism 107 is at the position limits 49a, 49b and 49c of FIG. 5, and an example thereof will now be described.

Figure 6:
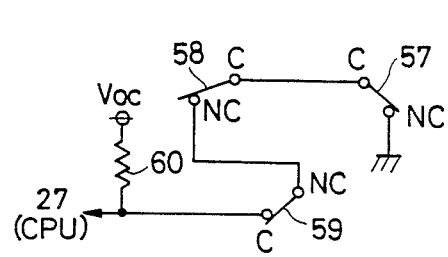
FIG. 6 shows an electrical connection in a case where microswitches are used in the second embodiment.

FIG. 6 shows an example of electrical connection in which a microswitches are used. In FIG. 6, Vcc designates a power source and the reference numeral 60 denotes a pull-up resistor. Microswitches 57, 58 and 59 are switches adapted to be closed to the NC side when the prism 107 is disposed outside the light beam 56 from the position of the position limits 49a, 49b and 49c in FIG. 5, and in this position, the CPU receives a low level signal. When the prism 107 is in a position crossing the light beam, one of the microswitches 57, 58 and 59 becomes OFF and a high level signal is input to the CPU 27. Thus, whether the prism 107 is within the light beam 56 can be judged.

We claim:

1. A laser applying apparatus provided with:
   a laser source means for providing laser light;
   setting means for setting an intensity of the laser light applied to a portion to be irradiated;
   first adjusting means having at least a portion disposed in said laser source means for selecting a stage of laser light intensity conforming to a value set by said setting means from among a plurality of stages of laser light intensity and causing it to be output from said laser source means; and
   second adjusting means disposed in an optical path of the laser light for adjusting the intensity of the laser light output from said laser source means to the intensity set by said setting means, by varying the light attenuation rate.

2. A laser applying apparatus according to claim 1, wherein said second adjusting means is a light attenuator comprising two polarizers one of which nearer to said laser source is rotatable and the other is fixed.

3. A laser applying apparatus according to claim 1, further provided with intensity detecting means for detecting the intensity of the laser light passed through said second adjusting means and wherein the light attenuation rate of said second adjusting means is set by the signal of said intensity detecting means.

4. A laser applying apparatus having:
   a laser source means for providing laser light;
   setting means for setting an intensity of the laser light applied to a portion to be irradiated;
   first adjusting means having at least a portion disposed in said laser source means for selecting a stage of laser light intensity conforming to a value set by said setting means from among a plurality of stages of laser light intensity and causing it to be output from said laser source means;
   second adjusting means disposed in an optical path of the laser light for adjusting the intensity of the laser light output from said laser source means to the intensity set by said setting means, by varying the light attenuation rate;
   intensity detecting means for detecting at a first time the intensity of the laser light passed through said second adjusting means;
   estimating means for estimating the intensity of laser light to be output at a second time, subsequent to the first time, from said laser source means to said portion to be irradiated; and
   calculating means for calculating the attenuation ratio of said second adjusting means from the estimated value produced by said estimating means and the set value of said setting means.

5. A laser applying apparatus according to claim 4, wherein said laser source means emits a pulse laser light.

6. A laser applying apparatus according to claim 5, wherein said estimating means finds the average value of the past several intensities of the pulse laser light detected by said detecting means and estimates the light intensity of the pulse laser light output next in said portion to be irradiated from said average value and the current value of said attenuation rate.

7. A laser applying apparatus having:
   a laser source means for providing laser light;

setting means for setting an intensity of the laser light applied to a portion to be irradiated;

first adjusting means having at least a portion disposed in said laser source means for selecting a stage of laser light intensity conforming to a value set by said setting means from among a plurality of stages of laser light intensity and causing it to be output from said laser source means;

second adjusting means disposed in an optical path of the laser light for adjusting the intensity of the laser light output from said laser source means to the intensity set by said setting means, by varying the light attenuation rate;

observation light applying means for applying an observation light for observing the portion to be irradiated to which the laser light is applied;

detecting means for detecting when said observation light applying means intersects the optical path of the laser light; and means for decreasing the intensity of the laser light output from said first adjusting means substantially when said detecting means detects said observation light applying means intersecting the optical path.

8. A laser applying apparatus according to claim 7, wherein the laser light is intercepted by shutter means provided in the optical path substantially when said detecting means detects said observation light applying means intersecting the optical path.

9. A laser ophthalmic apparatus having:

a laser source for providing laser light;

setting means for setting an intensity of the laser light applied to an eye to be examined;

first adjusting means having at least a portion disposed in said laser source means for selecting a stage of laser light intensity conforming to the value set by said setting means from among a plurality of stages of laser light intensity and causing it to be output from said laser source means; and second adjusting means disposed in an optical path of the laser light for adjusting the intensity of the laser light output from said laser source means to the intensity set by said setting means, by varying the light attenuation rate.

* * * * *

UNITED STATES PATENT AND TRADEMARK OFFICE
CERTIFICATE OF CORRECTION

PATENT NO. : 4,866,243

DATED : September 12, 1989

INVENTOR(S) : Toshio Sakane, et al

It is certified that error appears in the above-identified patent and that said Letters Patent is hereby corrected as shown below:

Column 1:

Line 36, "YA rod" should read --YAG rod--.

Column 6:

Line 36, "estimate" should read --estimated--.

Signed and Sealed this

Nineteenth Day of May, 1992

Attest:

DOUGLAS B. COMER

Attesting Officer

Acting Commissioner of Patents and Trademarks